United States Patent [19]

Shofner et al.

[11] Patent Number: 5,321,496
[45] Date of Patent: Jun. 14, 1994

[54] APPARATUS FOR MONITORING TRASH IN A FIBER SAMPLE

[75] Inventors: Frederick M. Shofner; Joseph C. Baldwin; Mark G. Townes; Youe-T Chu; Michael E. Galyon, all of Knoxville, Tenn.

[73] Assignee: Zellweger Uster, Inc., Knoxville, Tenn.

[21] Appl. No.: 762,905

[22] Filed: Sep. 19, 1991

Related U.S. Application Data

[63] Continuation-in-part of Ser. No. 493,961, Mar. 14, 1990, Pat. No. 5,270,787.

[51] Int. Cl.$^5$ .................. G01N 21/00; D01B 3/00
[52] U.S. Cl. .................................. 356/238; 19/200
[58] Field of Search ................... 356/238; 19/200

[56] References Cited

U.S. PATENT DOCUMENTS

| | | | |
|---|---|---|---|
| 4,512,060 | 4/1985 | Shofner | 19/200 |
| 4,631,781 | 12/1986 | Shofner | 19/200 |
| 4,686,744 | 8/1987 | Shofner | 19/200 |
| 4,839,943 | 6/1989 | Leifeld . | |

FOREIGN PATENT DOCUMENTS

| | | |
|---|---|---|
| 0226430 | 6/1987 | European Pat. Off. . |
| 2095828A | 10/1982 | United Kingdom . |

Primary Examiner—Richard A. Rosenberger
Assistant Examiner—K. P. Hantis
Attorney, Agent, or Firm—Luedeka, Hodges, Neely & Graham

[57] ABSTRACT

An apparatus for monitoring trash in a sample of trash particles and fibers includes scales for determining the weight of the sample which is transmitted to a computer. The sample is presented to a sensing volume and an optical sensor produces an output signal corresponding at least to the presence of the trash particle in the sensing volume. In one embodiment, the output signal is the waveform corresponding to light extinction caused by the presence of the particle in the sensing volume. In a second embodiment, image analysis of trash particles in a sensing volume provide output signals corresponding to the size, shape or composition of the particles. The computer receives the weight data and the output signal from the optical sensor and produces output data in the form of a count of at least a portion of the trash particles per unit weight of sample. The computer also outputs data in the form of or corresponding to the effective diameter, projected area and weight of the trash particles and count and weight of the fibers. In particular, the computer categorizes trash particles and outputs data for a particular category of particles.

15 Claims, 8 Drawing Sheets

APPARATUS FOR MONITORING TRASH IN A FIBER SAMPLE

This application is continuation-in-part of a U.S. application Ser. No. 07/493,961 filed Mar. 14, 1990, now U.S. Pat. No. 5,270,787.

SUMMARY OF THE INVENTION

The present invention relates to measurement of foreign matter in fiber samples. More specifically, methods and apparatus are provided for counting, sizing and categorizing visible foreign matter in cotton. These measurements are according to new definitions of foreign matter of trash.

Trash and dust in cotton originate at harvesting. A major objective of any cleaning process is to remove this "visible foreign matter" (VFM) and to minimize cleaning aggressiveness. Over recent years, throughputs of cotton ginning factories have dramatically increased. For World-Class textile mills, cleaning requirements have steadily increased because modern, high-production spinning machinery is less tolerant of trash and dust. Removing trash and dust is always at the further expense of fiber loss and damage. Obviously, optimization between trash and dust, nep and short fiber content must be achieved for every ginning and spinning process.

Trash and dust represent undesirable particles in textile fiber. Not only does this VFM affect yarn evenness and tenacity, it reduces manufacturing process efficiency.

Historically, trash and dust have been measured by slow gravimetric methods. That is, the VFM is removed and its weight as a percentage of the sample is reported. Such gravimetric methods cannot provide information on the count or size or shape or type of trash and dust particles. Gravimetric precision accuracy and speed becomes unacceptable for today's clean sliver, when the weight percent is often less than 0.1%, and for today's information technology driven ginning, spinning and marketing environment.

More importantly, the number of trash particles, along with their size, shape and type, is increasingly a better description of fiber value or processing performance than simple weight.

Thus, it is clear that more precise, more accurate, faster and more cost-effective measurements of trash or foreign matter, according to prior art definitions, are needed. But it is equally clear that additional measurements are needed. It is no longer adequate to report percentage weight of foreign matter at various processing points; it is also important to report the sizes and types or categories of trash (leaf, bark, grass, seed coat fragments, etc.), or how difficult the foreign matter is to remove (cleanability), or whether the trash or a specific category is detrimental to a given textile manufacturing process.

Accordingly, it is an object of this invention to provide new measurements of foreign matter in fiber samples. A fundamentally new physical parameter, counts of trash particles per gram of sample, is disclosed. Improved description of foreign matter and, thus, improved quality and profitability will result from widespread use of this parameter and its extensions to size, shape and type categories.

It is a further object to provide fundamentally different methods and apparatus for the measures of counts/gram, size, shape and type. These methods and apparatus embody means for presentation of individual entities of foreign matter to optical sensing means.

And it is an important result of this invention that improved measurement of percentage weight of foreign matter in fiber samples, the prior art descriptive parameter, can be provided with improved precision, accuracy and speed for clean fiber samples.

SUMMARY OF INVENTION

The present invention meets the foregoing and other objectives associated with monitoring trash by providing an apparatus in which a sample of trash particles and fibers is weighed and then processed to determine trash data. A presentation system, preferably a separator, air transport system and nozzle, presents substantially all of the trash particles in the sample to a sensing volume in condition for being optically sensed. An optical sensor senses substantially all of the trash particles as they are presented in the sampling volume and an output signal is produced that indicates at least the presence of a trash particle in the sampling volume. This output signal is transmitted to a computer that includes analog to digital converters for the purpose of receiving analog signals. Based on the sensor output signal, the computer determines at least a count of trash particles and calculates a count of trash particles per unit weight of the original sample. Then, the computer outputs data in the form of a count of trash particles per unit weight of sample.

In the preferred embodiment, the optical sensor senses the presence, and measures a characteristic, of each trash particle, where the characteristic corresponds to the size of the trash particle. One or more outputs (V) are produced by the optical sensor that correspond to such projected area. In general, the preferred processing means receives the output (V) and output data corresponding to the count and size of the trash particles. In particular, the processing means calculates a projected area (as hereinafter defined) of each trash particle based on the sensed characteristic (V) using a different equation for different size particles. Specifically, the processing means uses one equation for small particles and another equation for large particles, where the difference between small and large particles is defined by a predetermined threshold value of the sensed characteristic. In other words, if output (V) is smaller than the threshold, the particle is treated as a small particle. Otherwise, it is treated as a large particle.

In the preferred embodiment, the processing means also calculates a count of small particles per unit weight of sample (preferably, count/gram) and calculates a separate count of large particles per unit weight of sample. Both of the counts are also output as data.

Also, the weight of the trash particles correlates to the accumulated projected area. Thus, the preferred processing means also calculates and outputs the total predicted weight of trash in the sample and the visible foreign matter (VFM) percentage based on the accumulated projected area. In addition, the processing means calculates and outputs the mean projected effective diameter of trash particles. As used herein, "effective diameter" refers to a diameter determined experimentally using square meshes or sieves. Particles that will pass through a square mesh having X by X openings, but will not pass through the next smaller mesh having Y by Y openings, are said to have an effective diameter of $(X-Y)^{0.5}$. Projected area is the square of effective diameter and is later defined as "E-O" (Electro-optical) units.

In the preferred embodiment, a light detector is disposed to detect light produced by a source and, as a particle passes between the source and detector, the extinction of light is measured to produce an output (V). Other measurements may be made in addition to, or substitution for, extinction, such as back scattered and/or forward scattered light caused by the particle. Such measurements may be made at various angles and using different fields of view depending on the desired information. Such electro-optical techniques reveal additional characteristics of a particle including geometry or shape, fineness, composition and type. Using this information and known characteristics of trash, such as cotton trash, one may identify each particle as leaf, seed coat, grass, bark, etc. Thus, for example, one may output data indicating the number of trash particles per gram of sample (count/gram) where effective diameter is greater than 500 micrometers and that are "leaf." For another example, one may provide the count of trash particles per gram that are longer than 1,000 micrometers, thinner than 100 micrometers and whose $V_{40}/V_0$ ratio is less than 0.85 where $V_{40}$ represents 40° forward light scatter and $V_0$ represents light extinction at 0°, both with respect to the travel direction of light. In making such measurements, it will be appreciated that presentation of the entity for measurement facilitates or makes possible the counting, sizing and typing of entities such as trash particles.

BRIEF DESCRIPTION OF THE DRAWINGS

The present invention may best be understood by reference to the following Detailed Description of preferred embodiments when considered in conjunction with the Drawings in which.

DETAILED DESCRIPTION

Figure 1:
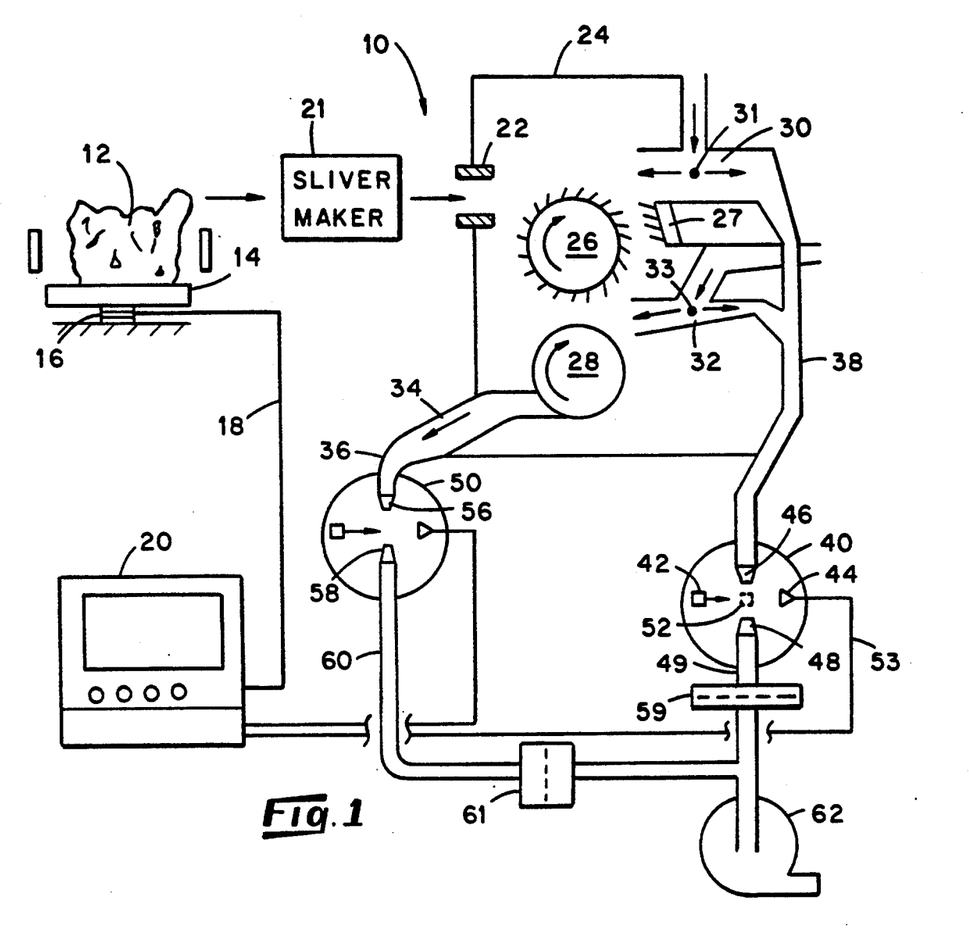
FIG. 1 is a block diagram of the trash monitoring apparatus.

Referring now to the drawings in which like reference characters designate like or corresponding parts throughout the several views, there is shown in FIG. 1 a trash monitoring apparatus 10 for monitoring trash in a fiber sample 12 that includes both fibers and trash. The sample 12 is first placed on a scales 14 where a pressure (or weight) sensitive transducer 16 produces a signal on line 18 that corresponds to the weight of the sample 12. The signal on line 18 is transmitted to a computer 20 which includes appropriate A to D converters for receiving the analog weight signal. The computer 20 calculates and stores the weight of the sample 12 based on the signal from line 18.

Next, the sample 12 is formed into an elongated configuration commonly referred to as a sliver by a mechanical sliver maker 21 or by hand, and the sliver is delivered through conduit 22 to an individualizer/separator 24 such as sold by Zellweger Uster, Inc. The fiber sample 12 engages separator wheels 26 and 28 and carding flats 27 and other elements known in the art within the separator 24 which separate the fibers from the trash. The trash is collected by conduits 30 and 32. As noted by the arrows within conduits 30 and 32, there is an airflow within conduits 30 and 32 proximate to the wheels 26 and 28 that will oppose the motion of particles ejected into conduits 30 and 32. This airflow is commonly referred to as a counterflow and the conduit is referred to as a counterflow slot. The counterflow air returns fibers thrown into the conduits 30 and 32, but the wheels impart a sufficient velocity to the trash particles that they overcome the counterflow and reach turning points 31 and 33 where the trash particles are then entrained in an airflow within conduits 30 and 32 traveling in an opposite direction from the counterflow. It is clear that turning points 31 and 33 represent small volumes of space within conduits 30 and 32 wherein the trash particles are either returned to the cylinders 26, 28 or carried out. It is also clear that the size of the trash particles which are carried out can be adjusted.

The lint (fiber) is collected by conduit 34 and delivered to a conduit 36 within which there is a vacuum driven airstream. Likewise, a vacuum driven airstream within a conduit 38 receives and entrains the trash particles from conduits 30 and 32. The separator 24 is designed to separate and individualize both the trash particles and the fibers such that substantially all of the trash particles are delivered substantially one at a time to conduit 38 and substantially all of the fibers are delivered substantially one at a time to conduit 36. While aeromechanical separation of the trash particles from the fibers with delivery to separate airflows is preferred, it will be recognized that the entities of the sample 12 could be individualized mechanically, but combined and delivered to a single airflow, and then distinguished or typed by optical means. In other words, the entities could be separated into trash and fiber categories by optical means.

The trash particles in conduit 38 are delivered to an optical sensor 40 where they are presented for measurement by a nozzle 46 as they pass through light generated by a light source 42 and detected by an optical detector 44. The particles are then collected by suction nozzle 48 and entrained in a suction driven airstream within conduit 49. As the trash particles pass through the sensor 40, they pass through a sensing volume 52 in which they are presented in a substantially random orientation. Thus, while nozzle 46 accelerates the particles and nozzle 48 decelerates the particles, the nozzles are designed to present the particle within the sensing volume 52 in a substantially random orientation. The light sensed by sensor 44 is transmitted in the form of a voltage signal on line 53 which transmits the signal to the computer 20 which has appropriate A to D converters for receiving and inputting the signal into the computer 20. In the preferred mode, sensor 44 and light source 42 are arranged to detect the extinction of light caused by a particle passing through the sensing volume 52. Light scattering may also be used, as can any combination. Although the preferred embodiment is described primarily with regard to detection of light extinction, sensor 44 will be understood to represent a combination detector that detects forward light scattering, backscattering of light and extinction of light caused by particles passing through sensing volume 52.

A similar electro-optical sensor 50 is provided at conduit 36 to sense the optical characteristics of the fibers as they pass through the sensor 50. In this configuration, one may feed a single sample and obtain multiple data (SS/MD) products on both fibers and trash. Sensors 50 and 40 are substantially the same except that sensor 50 includes an injection nozzle 56 and a suction nozzle 58 that are designed to orient the fiber as it passes through the sensor 50. The ability to orient the fiber is particularly useful when measuring fibers but is not absolutely necessary. Particularly, in the case of trash, it is not necessary to orient the trash in any particular angular position prior to its passing into the sensing volume 52. In fact, it is preferred to present trash in a substantially random orientation.

Sensor 40 is connected via conduit 49, and sensor 50 is connected via conduit 60 to a vacuum pump 62 that provides the suction or vacuum necessary for establishing the airstreams as described above. A filter 59 is disposed in conduit 49 upstream of pump 62 for collecting all trash particles and a filter 61 is disposed in conduit 60 for collecting all fibers. For any given sample 12, the fibers and trash may be separately recovered from the filters 59 and 61 for manual analysis, such as being weighed in scales 14. This manual analysis is primarily used to calibrate the instrument as to measurements and calculations based on outputs from sensors 40 and 50, verify such optical measurements or supplement them.

Figure 2:
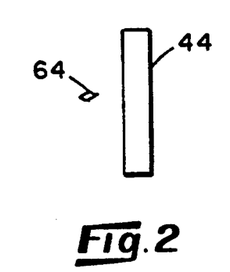
FIG. 2 illustrates a small trash particle and a sensor.

Referring now to FIG. 2, there is shown a small particle 64 that is approaching the optical sensor 44. It will be noted that the small particle 64 has an area that is substantially smaller than the width of sensor 44. Thus, as the particle 64 passes in front of the sensor 44, it should be appreciated that the light extinguished by the particle 64 likely will be dependent upon the projected area of the particle.

Figure 3:
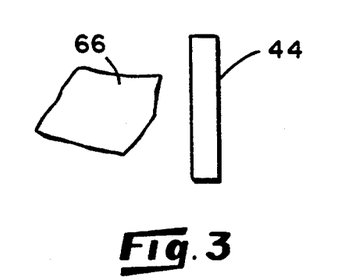
FIG. 3 illustrates a large trash particle and a sensor.

Referring to FIG. 3, a large particle 66 is shown approaching the sensor 44. When particle 66 passes before the sensor 44, it will be appreciated that the particle will span the sensor 44. Thus, the amount of light extinguished by the particle 66 that would have otherwise been sensed by sensor 64 likely will be proportional to the effective diameter of the particle 66.

Figure 4:
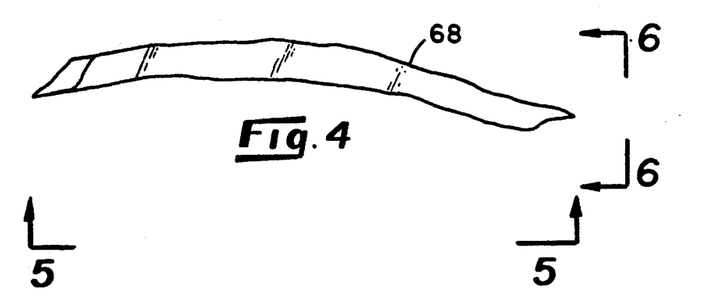
FIG. 4 is a side edge view of a trash particle.
Figure 5:
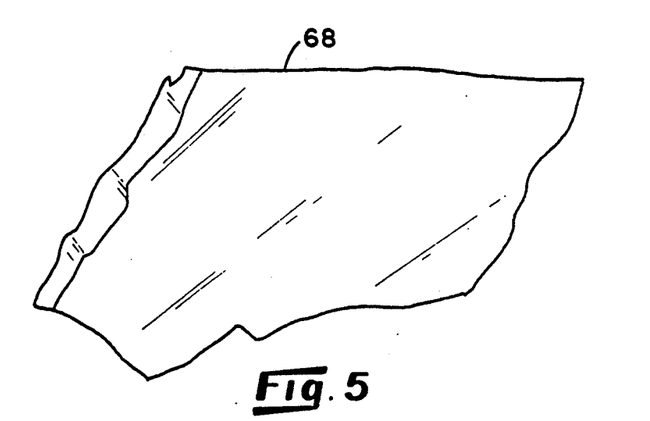
FIG. 5 is a top plan view of a trash particle.
Figure 6:
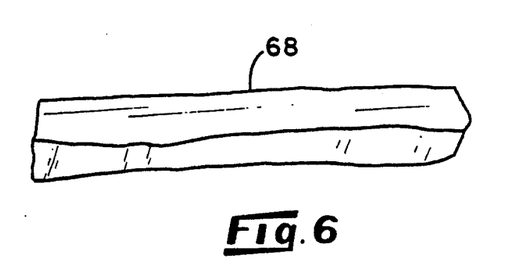
FIG. 6 is a front edge view of a trash particle.

Referring now to FIGS. 4, 5 and 6, a typical trash particle 68 is shown in a side edge view, a top plan view, and a front end edge view, respectively. Most trash particles have a flake shape something like that shown in the figures and, thus, it will be appreciated that the view or presentation of a trash particle 68 will vary dramatically depending upon the orientation of the flake when it passes the sensor. This might suggest that data, particularly light extinction data, produced by sensor 40 would be of limited usefulness.

Figure 7:
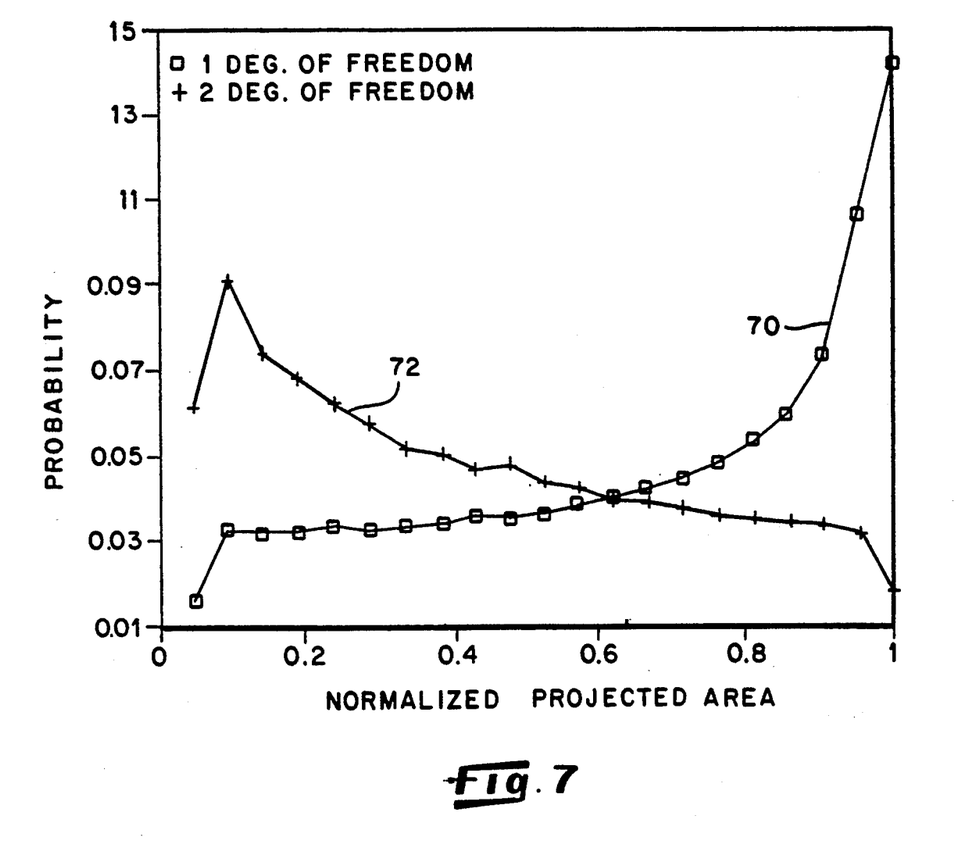
FIG. 7 is a graph showing probability on the Y axis and normalized projected area of a trash particle on the X axis.

In FIG. 7, a graph is shown indicating the probability that a trash particle, such as particle 68, will present itself in the normalized or perpendicular orientation as shown in FIG. 5. A curve 70 shows the probability of various orientations of a trash particle when it is allowed to rotate freely on one axis, and the normal view is predicted to occur slightly more than 14% of the time. Whereas, a view of one-tenth of the normalized projected area is predicted to occur only about 3% of the time.

When the trash particle is allowed to rotate freely on two perpendicular axes, the normal view of the trash particle 68 is predicted by curve 72 to occur less than 2% of the time, while a presentation of approximately 10% of the normalized projected area is predicted to occur about 9% of the time. Likewise, a view of 15% of the normalized projected area would occur about 7.5% of the time, while a 20% view would appear about 7% of the time. Based on curve 72, in the case of a particle presented in a random orientation, one should expect to rarely see a normal view of the particle. Thus, again, one might expect that the presentation of substantially randomly oriented trash particles to an optical sensor would produce a detection signal that did not contain useful size information because one would rarely be looking at normal incidence to the particle.

Figure 8:
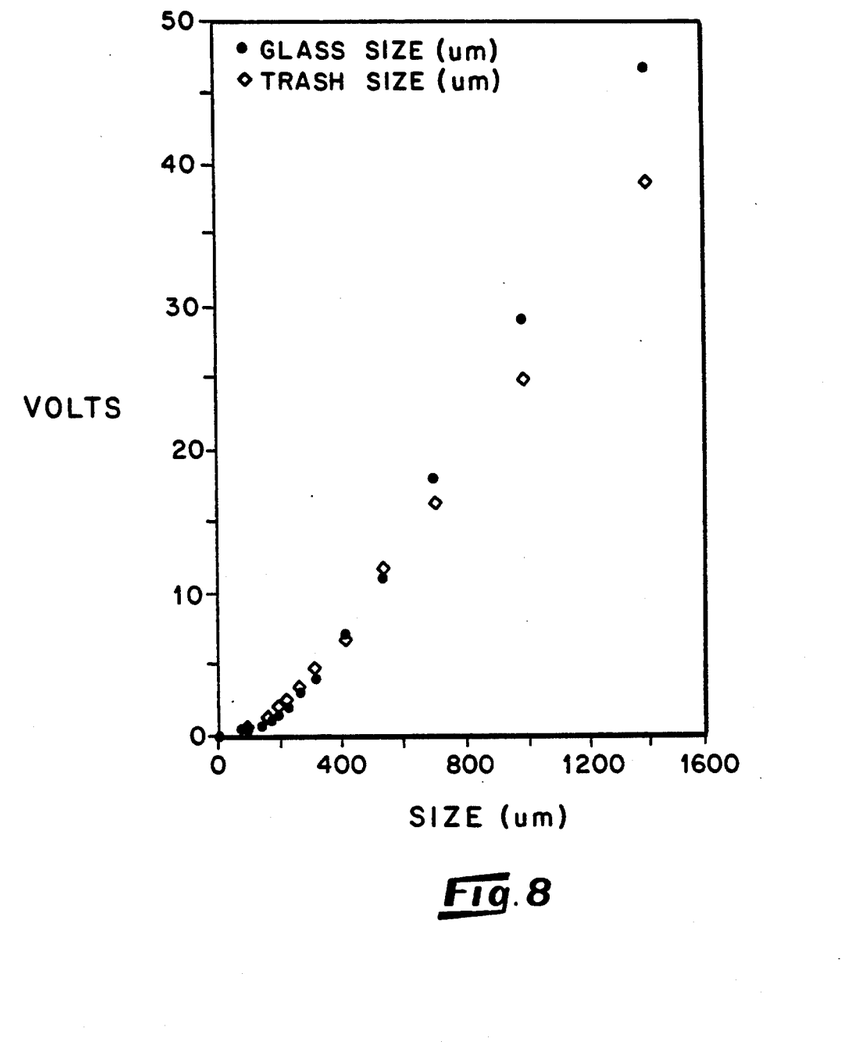
FIG. 8 is a graph showing the diameter of the particle on the X axis with the Y axis showing the voltage produced by the particle as it was presented to a sensor.

However, experimental results, which are shown in FIG. 8, show that the light extinction output of sensor 44 will correlate well with a particle's effective diameter and, thus, will also correlate well with the particle projected area. On the Y axis of FIG. 8, the average of peak voltages from sensor 44 is graphed against particle diameter on the X axis. The actual effective diameter of the particles were determined for the purpose of this test by manually passing the particles through screen meshes of increasingly small openings. The circular symbols graphically show data for glass beads, which are spherical, and the diamond symbols graphically show data for trash particles. It will be appreciated that the average of peak voltages is correlating well to the diameter for both trash particles and glass spheres (The voltage signals shown in FIG. 8 are actually two amplifiers, the higher sensitivity having gain 12.5 times the lower. The readings are normalized to the higher gain stage. Two stages are required to cover the wide dynamic range.)

Figure 9:
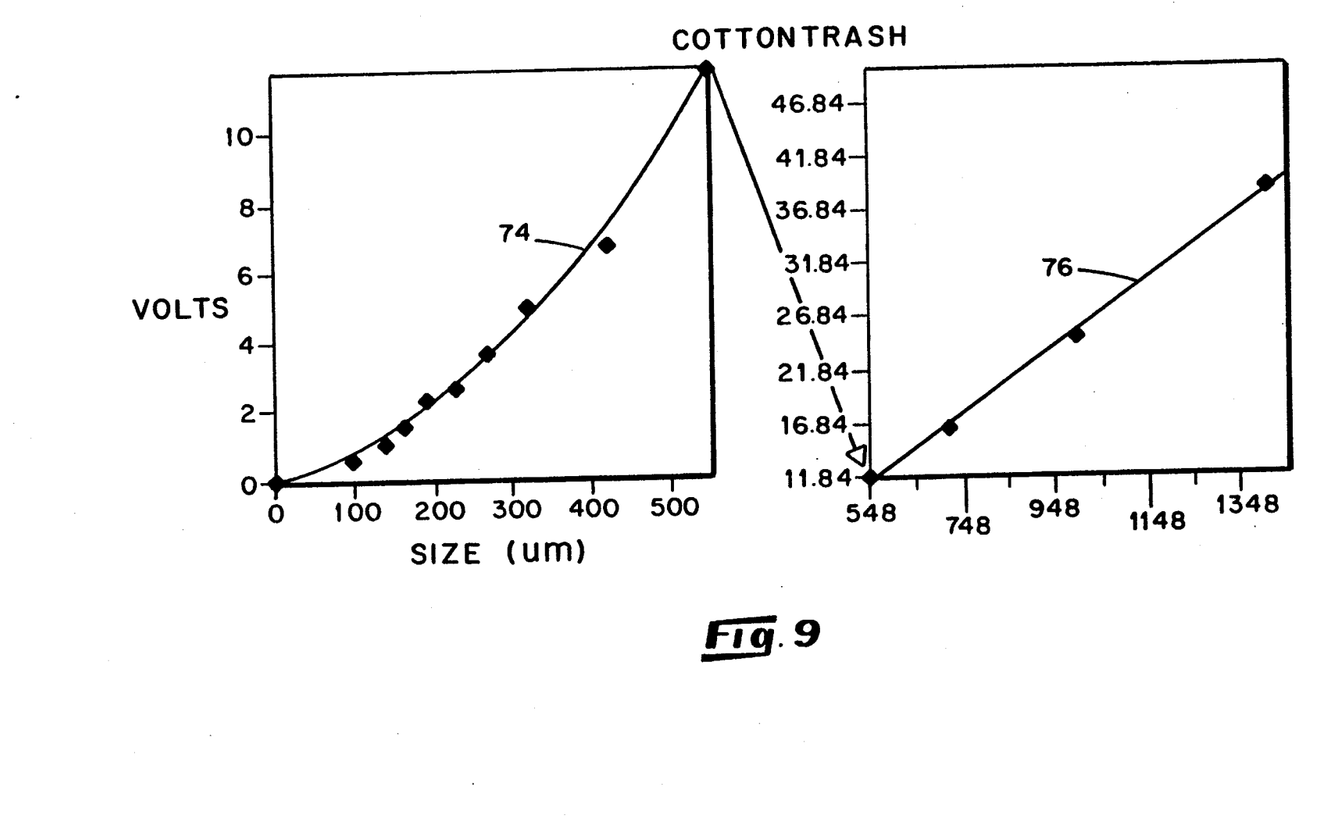
FIG. 9 is a split graph showing information similar to that shown in FIG. 8.

In FIG. 9, curve portions 74 and 76 are similar to the curves of FIG. 8, but the curve portions have been broken apart for purposes of clarity. By reference to FIG. 9, it will be appreciated that the functional relationship between the output of sensor 44 and particle size is different for small and large particles. For small particles, the sensor 44 output voltage (V) is related to particle size by an equation of the form $V = a + bX + cX^2$, where X is a one dimensional particle size such as an effective diameter. Specifically, for cotton trash particles smaller than about 488 microns the relationship may be defined as follows: $V = 0.0000303X^2 + 0.00475X - 0.0403$. For large particles, the relationship is defined by an equation having the form $V = mX + b$. Specifically, for cotton trash particles having a diameter greater than 488 microns, the relationship is defined by the following formula: $V = 0.0313X - 5.78$.

To quickly summarize: individual trash particles, as described in FIGS. 2-6 and the text related thereto, produce signals on lines 53 when they move through optical sensor 40 of FIG. 1. The computer 20 at least counts these signals which of course represent trash particles, and in combination with the sample weight, produce a new, basic data product of counts per gram of sample.

But these signals on lines 53 not only represent the counts per gram of trash particles, they contain information about the size, shape, composition and orientation. See co-pending application, Ser. No. 07/493,961. This detailed, electro-optical information could be used to determine the weight of each particle Multiplication by the counts/gram in a specific size range and summation over all particle size ranges would give the total weight of trash particles. Division by sample weight then leads to a prediction of VFM %.

Fortunately, our investigations have revealed a simpler and more elegant method to predict VFM % using the average extinction mode signal only. FIGS. 8 and 9 represent precisely the necessary and sufficient calibration results on samples with known size, shape and composition characteristics. Orientation is also inherently included in the calibration.

The first step in measurement of an unknown sample is to calculate an effective diameter D for each trash voltage signal Specifically, the computer 20 of FIG. 1 uses the extinction detector output of sensor 40 to calculate a one dimensional size measure D (effective diameter) for each particle. For example, from FIGS. 8 or 9 a peak extinction voltage of 9.5 volts corresponds, in the average, to trash particles having an effective diameter of D=488 micrometers. Importantly, this average includes all effects of size, shape, composition and orientation. This transform of voltage to effective diameter D from FIG. 8 is handled by computer 20 via a look-up table or via quadratic and linear equations as described above.

The second step is to calculate the E-O units according to this definition:

$$\text{E-O units} = (D/1,000)^2$$

This has the interpretation of projected area in square millimeters for each trash particle. The third step is to sum the E-O unit contributions of all particles in the sample.

Figure 10A:
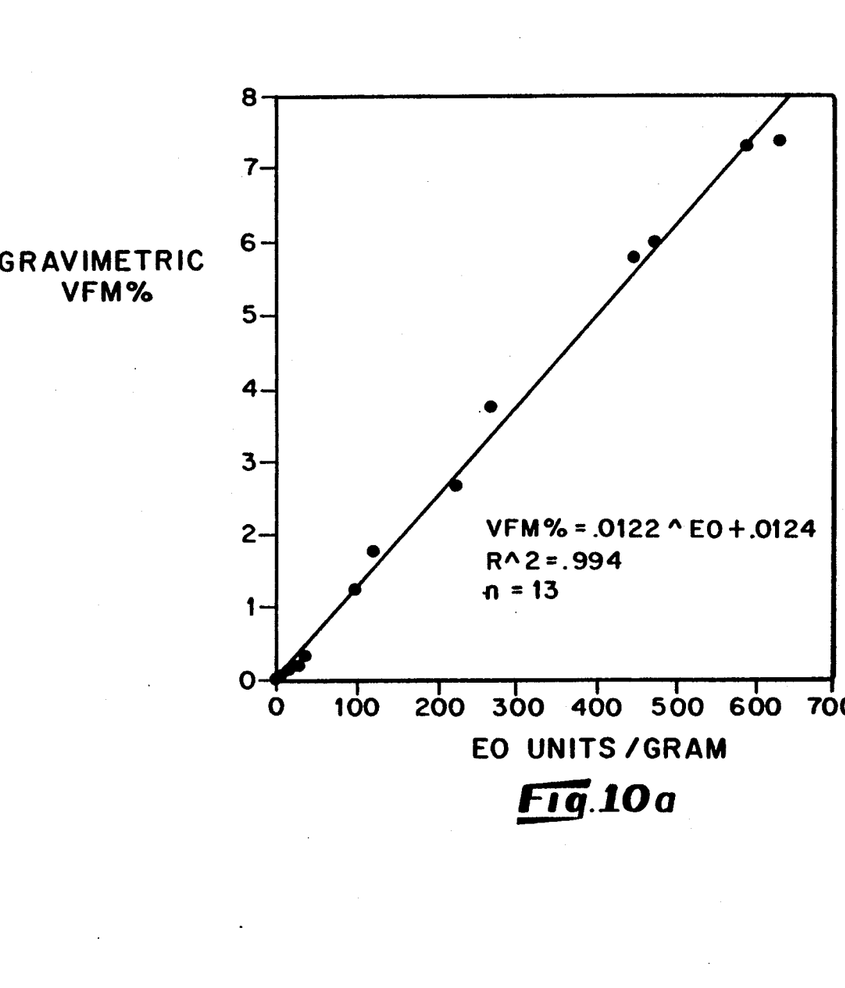
FIGS. 10a and 10b are a graph and chart, respectively, showing the correlation between the projected area per gram as measured by the present invention and the visible foreign matter percentage determined manually.
Figure 10B:
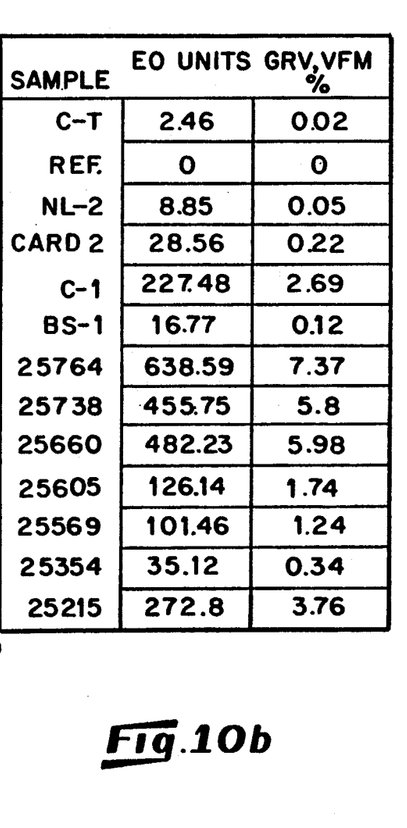

As a confirmation that this method is valid for trash, consider FIGS. 10a and b. The Y axis of FIG. 10a represents the usual gravimetric weight of visible foreign matter, VFM %. The trash material was captured with filter 59 of FIG. 1.

E-O units on the X axis, for the wide range of trash contents covered, are seen to be highly correlated with VFM %. This result supports the hypothesis that the weight per trash particle is proportional to its E-O units. This hypothesis is also plausible on physical grounds. Finally, the total E-O units per gram have an intuitively satisfying interpretation: total E-O units in square millimeters represent the projected area of the trash removed from one gram of sample.

Figure 11:
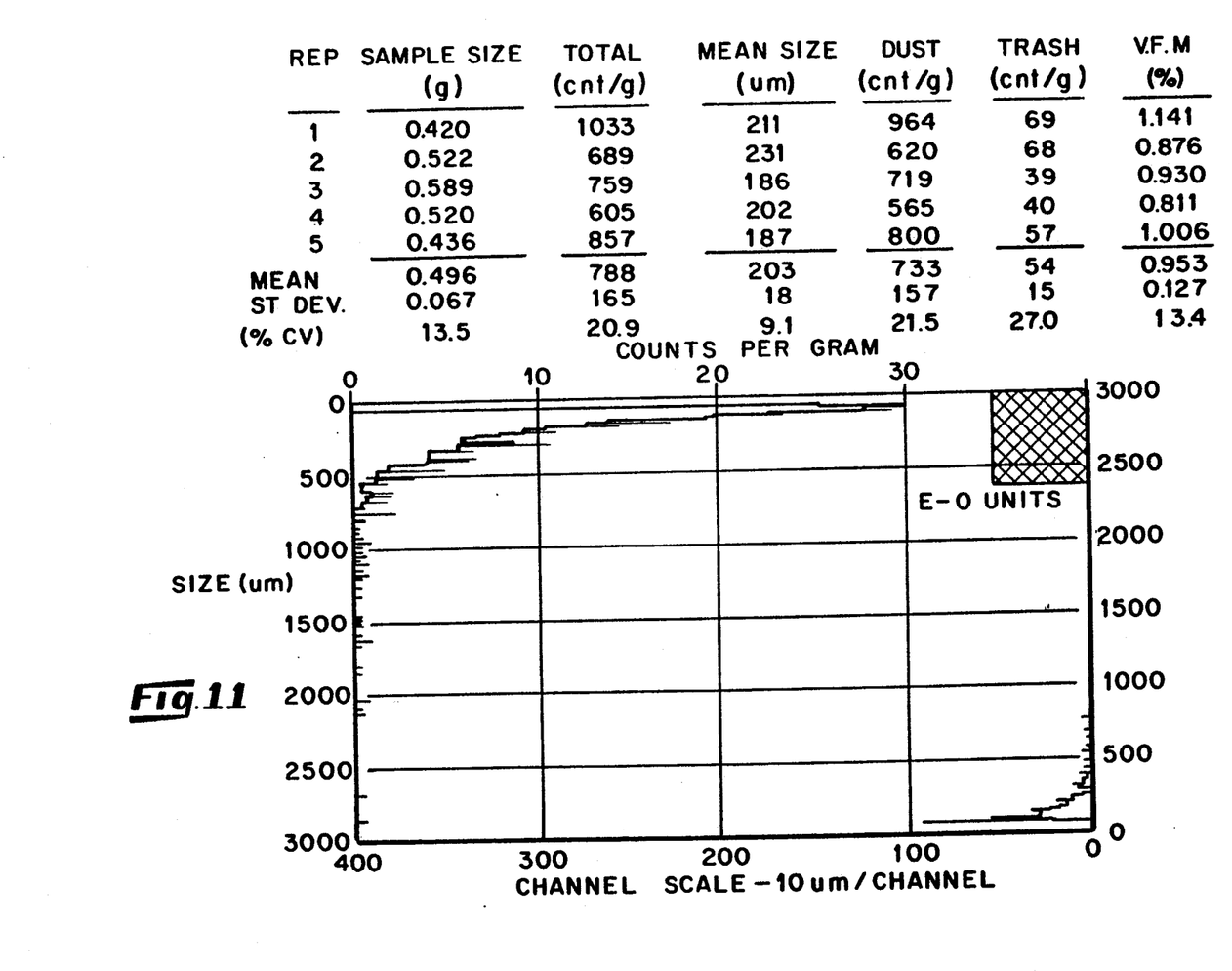
FIG. 11 is an example of typical output from the apparatus.

Referring now to FIG. 11, a typical output for five replicate samples of cotton fiber is shown. The first column entitled "Rep" shows the sample number or the repetition number. Under "Sample Size," the weight of the original cotton sample is given in grams. In the next column marked "Total," there is shown a count of trash particles per gram of original sample. In the next column, the "Mean Size," the mean effective diameter, of all trash particles for each sample, is shown in micrometers. Next, there is a column of "Dust" information shown in counts per gram. The computer 20 determines this number by counting the number of particles below a certain size (having a sensor output (V) smaller than a threshold) and dividing that count by the total weight in grams of the original sample. In the next column marked "Trash," there is an indication of the count per gram of particles greater than a predetermined size (having a sensor output (V) greater than a threshold). In cotton, particles having a mean size of less than 500 micrometers are generally considered dust and particles having a greater size are generally considered trash. Thus, in the preferred embodiment, there is an output for both dust and trash. However, it should be remembered that the term "trash", as when used in a general context herein, is referring to any non-fiber matter in the sample and thus includes dust and trash definitions above. This confusing terminology results from earlier measurement means and definitions and is, unfortunately, prevalent in the industry. In the last column, there is shown a calculated visual foreign matter percentage (VFM), the traditional unit of measure of trash in cotton fibers. The calculations are made on the basis of electro-optical units described above.

The bottom three numbers of each of the aforementioned columns show the mean of the five repetitions, the standard deviation, and the percent CV.

In the lower portion of the display shown in FIG. 11, there are two graphs showing count per gram on the X axis and size (effective diameter) on the Y axis. The first graph in the top left-hand corner uses the scale shown on the left and upper sides of the graph. The second graph shown in the lower right-hand corner uses the scales shown on the lower and right sides of the display. These graphs show the size distribution of the trash particles in a sample of fibers, but the data have been normalized to counts per gram of sample for each particle size. In the upper right-hand corner a graphical representation, a square, is shown representing E-O units which represent the projected area of the trash in a sample.

The above-described output is exemplary of the type of output provided by apparatus 10. It is noted that the count per gram of trash was given for the entire sample and for particular categories of trash, namely, size categories. Similarly, counts of trash per gram may be provided for other categories or types of trash or sample For example, the computer 20 also receives electro-optical data from sensor 50 on the clean fibers and electro-optically determines count and weight Thus, apparatus 10 may output counts of trash per count of clean fiber or counts of trash per gram of clean fiber as alternative outputs.

Figure 12:
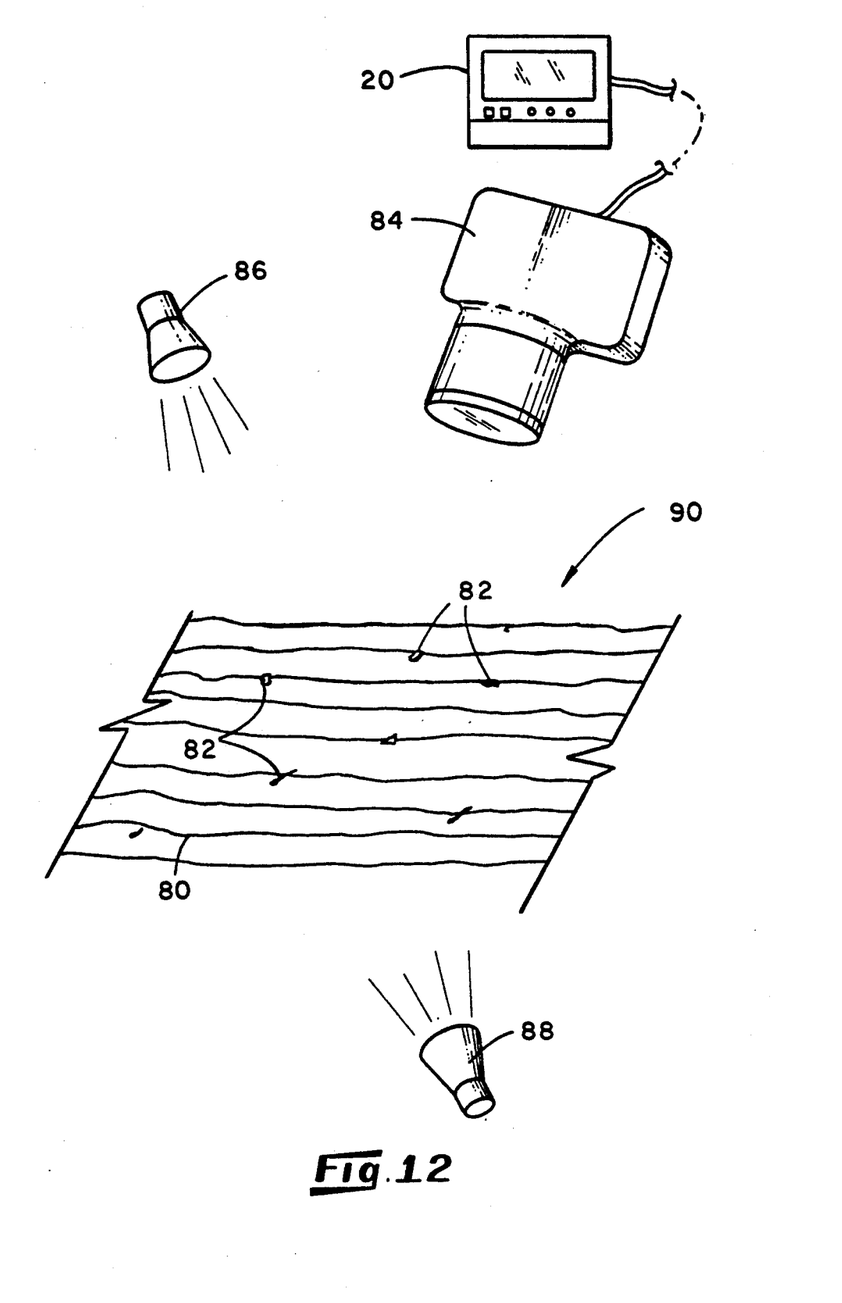
FIG. 12 shows an alternate embodiment utilizing a video camera viewing a thin web of fibers and trash.

Although the present invention has been described primarily with respect to the apparatus shown in FIG. 1, it will be understood that the key aspects of the invention are not limited in any respect to this particular apparatus. For example, while it is preferred to separate the trash particles from the fibers and measure them separately in a random presentation, it will be understood that other apparatus could be used to achieve the presentation. For example, as shown in FIG. 12, the fibers 80 and the trash 82 are presented together in a thin planar format. In such case, the fibers and trash would be sufficiently dispersed so that the trash is individualized and the layer of fibers is sufficiently thin in the sensing volume so that all trash particles may be viewed by camera. The area of sample 90 viewed by the camera 84 and the depth of the sample define the sensing volume in this embodiment, and the camera 84 views substantially all of the trash in the sensing volume as the sample 90 is presented. The camera is to be understood as providing image information within and out-side the visible spectrum. Specifically included are near infrared imaging means and provision of images at a multiplicity of wavelengths of light. Illumination is provided by one or more lights 86 above the sample 90 and one or more lights 88 below the sample, as desired. In this embodiment, conventional digital image analysis techniques are used first to identify all objects in the viewing area that have a geometric configuration and projected area sufficient to possibly constitute trash. Neps will usually meet this criteria and, thus, all objects must be further analyzed to reject fibrous objects, such as shiny neps or mature neps. Once the neps have been rejected, the remaining objects are counted and the computer 20 determines the projected area of each particle by counting the discrete picture elements (pixels) occupied by the trash particles 82. Once the count and projected area have been determined, the other desired data may be calculated in the manner previously described.

Finally, it is useful to note, in the new data product of counts of trash particles per gram of sample, that the weight of the fiber sample may be also determined electro-optically by the fiber sensor 50 in FIG. 1, according to provisions of the co-pending application.

We claim:

1. An apparatus for monitoring trash in a sample of trash particles and fibers comprising:
   weighing means for determining the weight of the sample and for producing weight data in weight units;
   a sensing volume;
   presentation means for presenting substantially all trash particles in the sample to said sensing volume in condition for being optically sensed;
   optical sensing means for sensing substantially all of trash particles as the trash particles are presented in said sensing volume and for producing an output signal corresponding at least to the presence of a trash particle in the sensing volume; and
   processing means for receiving the weight data and the output signal of said optical sensing means, for determining a count of at least a portion of the trash particles, for dividing the count by the weight of the sample and for outputting data in the form of counts of trash particles per unit weight of sample.

2. The apparatus of claim 1, wherein:
   said optical sensing means further optically senses both the presence of a trash particle and a characteristic corresponding to the projected effective diameter of the trash particle, said optical sensing means further producing an output (V) that corresponds to the sensed characteristic; and
   said processing means further operates to output data corresponding to the count and the sensed characteristic of the trash particle.

3. The apparatus of claim 2, wherein said processing means further calculates a projected area of each trash particle based on the sensed characteristic of each trash particle.

4. The apparatus of claim 2, wherein said processing means further calculates the projected effective diameter of the trash particles that produce a sensor output (V) above a predetermined threshold based on a formula in the form of: $V = mX + b$, and calculates a projected effective diameter of trash particles that produce a sensor output (V) below the predetermined threshold based on a formula of the form: $V = aX^2 + cX + d$, where a, b, c, d and m are constants and X is the projected effective diameter of each trash particle.

5. The apparatus of claim 4, wherein said processing means further predicts the weight of at least a portion of the trash particles based on the sensed characteristic of each particle in said portion and the count of particles in said portion.

6. The apparatus of claim 4, wherein said processing means predicts the visible foreign matter (VFM) percentage based on the count and the sensed characteristics of substantially all of the trash particles.

7. The apparatus of claim 2, wherein said processing means calculates a size for each trash particle based on the sensed characteristic, calculates a first count per weight of sample for trash particles in a first size range, calculates a second count per weight of sample for trash particles in a second size range, and outputs said first and second counts per weight of sample.

8. The apparatus of claim 7, wherein said first size range comprises trash particles having a sensed characteristic smaller than a predetermined value which corresponds to the largest trash particle that may be considered dust.

9. The apparatus of claim 2, wherein said processing means counts the trash particles that produce a sensed characteristic that falls within a predetermined range, calculates a count per weight of sample for trash particles having a sensed characteristic within a predetermined range, and outputs said count per weight of sample.

10. The apparatus of claim 2, wherein said processing means calculates a mean size value for substantially all of the trash particles in the sample and outputs the mean size value.

11. The apparatus of claim 1, further comprising:
    said processing means categorizing the trash particles into at least one separate category, counting the trash particles in the separate category to produce a categorized count and outputting data corresponding to said categorized count.

12. The apparatus of claim 11, wherein said data comprises a categorized count per weight of sample.

13. The apparatus of claim 1, further comprising:
    means for determining a characteristic of only the fibers, producing fiber data, and inputting the fiber data into the processing means; and
    said processing means calculating and outputting data in the form of counts as a function of the fiber data.

14. The apparatus of claim 13, wherein said characteristic is the count of fibers and said processing means calculates and outputs data in the form of count of trash per count of fiber 15. The apparatus of claim 13, wherein said characteristic is clean fiber weight and said processing means calculates and outputs data in the form of counts of trash per weight of clean fiber.

* * * * *